United States Patent
Matsui et al.

(10) Patent No.: US 6,893,832 B2
(45) Date of Patent: May 17, 2005

(54) METHOD FOR QUANTIFYING CHOLESTEROL IN HIGH DENSITY LIPOPROTEIN

(75) Inventors: Hiroshi Matsui, Gosen (JP); Yasuki Ito, Gosen (JP); Shuichi Ohara, Gosen (JP); Akira Fujiwara, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 47 days.

(21) Appl. No.: 10/190,793

(22) Filed: Jul. 9, 2002

(65) Prior Publication Data

US 2002/0192732 A1 Dec. 19, 2002

Related U.S. Application Data

(62) Division of application No. 09/117,806, filed as application No. PCT/JP97/04442 on Dec. 4, 1997.

(30) Foreign Application Priority Data

Dec. 9, 1996 (JP) .............................................. 8-344649

(51) Int. Cl.[7] ........................... C12Q 1/60; C01N 33/92
(52) U.S. Cl. .............................. 435/11; 435/25; 435/28; 436/71; 436/169; 436/170; 436/824
(58) Field of Search .............................. 435/11, 25, 28; 436/71, 169, 170, 824

(56) References Cited

U.S. PATENT DOCUMENTS 4,851,335 A   7/1989 Kerscher et al.
5,215,886 A * 6/1993 Patel et al. ................... 435/11
5,320,968 A   6/1994 Seman

FOREIGN PATENT DOCUMENTS

| JP | 58165800 A | 9/1983 |
| JP | 62069999 A | 3/1987 |
| JP | 63126498 A | 5/1988 |
| JP | 07-280812 A | 10/1995 |
| JP | 7301636 | 11/1995 |
| JP | 8116996 A | 5/1996 |
| JP | 08-201393 A | 8/1996 |
| JP | 09000299 | * 7/1997 |
| WO | WO 92/21015 | 11/1992 |
| WO | WO 97/00971 | 9/1997 |

* cited by examiner

*Primary Examiner*—Samuel Barts
*Assistant Examiner*—Howard V. Owens
(74) *Attorney, Agent, or Firm*—Birch, Stewart, Kolasch & Birch, LLP

(57) ABSTRACT

Disclosed is a method for quantifying cholesterol in HDL, which does not require complex fragmentation and separation operations, and by which the HDL cholesterol in test samples containing HDL and other lipoproteins such as low density lipoprotein (LDL), very low density lipoprotein (VLDL) and chylomicron (CM) may be quantified selectively, simply and accurately. The method for quantifying cholesterol in high density lipoprotein comprises a first step of erasing cholesterol in lipoproteins other than high density lipoprotein in a test sample, and a second step of adding a surfactant which specifically acts on high density lipoprotein to the product of the first step and enzymatically quantifying cholesterol in high density lipoprotein.

4 Claims, 3 Drawing Sheets

METHOD FOR QUANTIFYING CHOLESTEROL IN HIGH DENSITY LIPOPROTEIN

This application is a divisional of co-pending application Ser. No. 09/117,806, filed on Aug. 6, 1998 and for which priority is claimed under 35 U.S.C. § 120. application Ser. No. 09/117,806 is the national phase of PCT International Application No. PCT/JP97/04442 filed on Dec. 4, 1997 under 35 U.S.C. § 371. The entire contents of each of the above-identified applications are hereby incorporated by reference. This application also claims priority of Application No. 344649/96 tiled in Japan on Dec. 9, 1996 under 35 U.S.C. § 119.

TECHNICAL FIELD

The present invention relates to a method for quantifying cholesterol in high density lipoprotein (hereinafter also referred to as "HDL")

BACKGROUND ART

It is known that HDL relates to removal of cholesterol accumulated in cells because it receives cholesterol from various tissues including walls of blood vessels with arterial sclerosis, so that HDL is useful for estimating the risk for various arterial sclerosises including coronary artery sclerosis, and that its blood level is an indicator for the risk of onset of arterial sclerosis.

Methods for measuring cholesterol in HDL include a method in which HDL is separated from other lipoproteins by ultracentrifugation and then the HDL is measured; and a method in which the cholesterol in HDL is separated by electrophoresis, then the lipid is stained, and the intensity of the generated color is measured. However, these methods are complex or a number of samples cannot be assayed, so that they are not commonly used.

The method for measuring the cholesterol in HDL, which is generally used in the field of clinical test is the method in which a precipitating agent is added to the sample so as to coagulate the lipoproteins other than HDL, removing the coagulated lipoproteins by centrifugation, and the cholesterol in the resulting supernatant containing HDL alone is measured. Although this method is simpler than the ultracentrifugation method and the electrophoresis method, it is not satisfactorily simple because it comprises addition of the precipitating agent and subsequent separation, and a comparative large amount of sample is needed.

On the other hand, methods in which the cholesterol in HDL is separately quantified by using enzymes have been proposed. For example, a method is known, which comprises the steps of preliminarily coagulating the lipoproteins other than HDL by an antibody and polyanion, enzymatically reacting the cholesterol in HDL alone, inactivating the enzyme and simultaneously re-dissolving the coagulated mass, and measuring the absorbance of the resulting solution (Japanese Laid-open Patent Application (Kokai) No. 6-242110). However, this method has a problem in that it is necessary to add reagents at least three times, so that this method can be practiced only by the limited analyzing apparatuses. Therefore, this method is not widely used.

Other methods include a method in which an enzyme reaction is carried out in the presence of a bile salt or a nonionic surfactant (Japanese Laid-open Patent Application (Kokai) No. 63-126498); a more recently developed method in which the cholesterol in HDL is specifically trapped by chemically modified cholesterol esterase and/or cholesterol oxidase in the presence of a clathrate compound such as cyclodextrin (Japanese Laid-open Patent Application (Kokai) No. 7-301636); and a method in which the lipoproteins other than HDL are made into aggregates or complexes and then the cholesterol in HDL is trapped by an enzyme reaction (Japanese Laid-open Patent Application (Kokai) Nos. 8-131197 and 8-201393). However, with these methods, the results for certain samples are different from the results by the precipitation method, so that their specificities are problematic.

DISCLOSURE OF THE INVENTION

An object of the present invention is to provide a method for quantifying cholesterol in HDL, which does not require complex fragmentation and separation operations, and by which the HDL cholesterol in test samples containing HDL and other lipoproteins such as low density lipoprotein (LDL), very low density lipoprotein (VLDL) and chylomicron (CM) may be quantified selectively, simply and accurately.

The present inventors intensively studied to discover that surfactants which act on HDL but substantially do not act on other lipoproteins exist. The present inventors further discovered that HDL cholesterol in test samples containing HDL and other lipoproteins may be selectively, simply and accurately quantified by selectively erasing the cholesterol in the lipoproteins other than the high density lipoprotein in the test sample and then enzymatically quantifying the cholesterol originated from HDL in the presence of the above-mentioned surfactant, thereby completing the present invention.

That is, the present invention provides a method for quantifying cholesterol in high density lipoprotein, comprising a first step of erasing cholesterol in lipoproteins other than high density lipoprotein in a test sample, and a second step of adding a surfactant which specifically acts on high density lipoprotein to the product of the first step and enzymatically quantifying cholesterol in high density lipoprotein.

By the method of the present invention, the cholesterol in HDL in a test sample containing HDL and other lipoproteins such as LDL, VLDL and CM may be quantified selectively, simply and accurately, without complex fragmentation and separation operations.

BEST MODE FOR CARRYING OUT THE INVENTION

Figure 1:
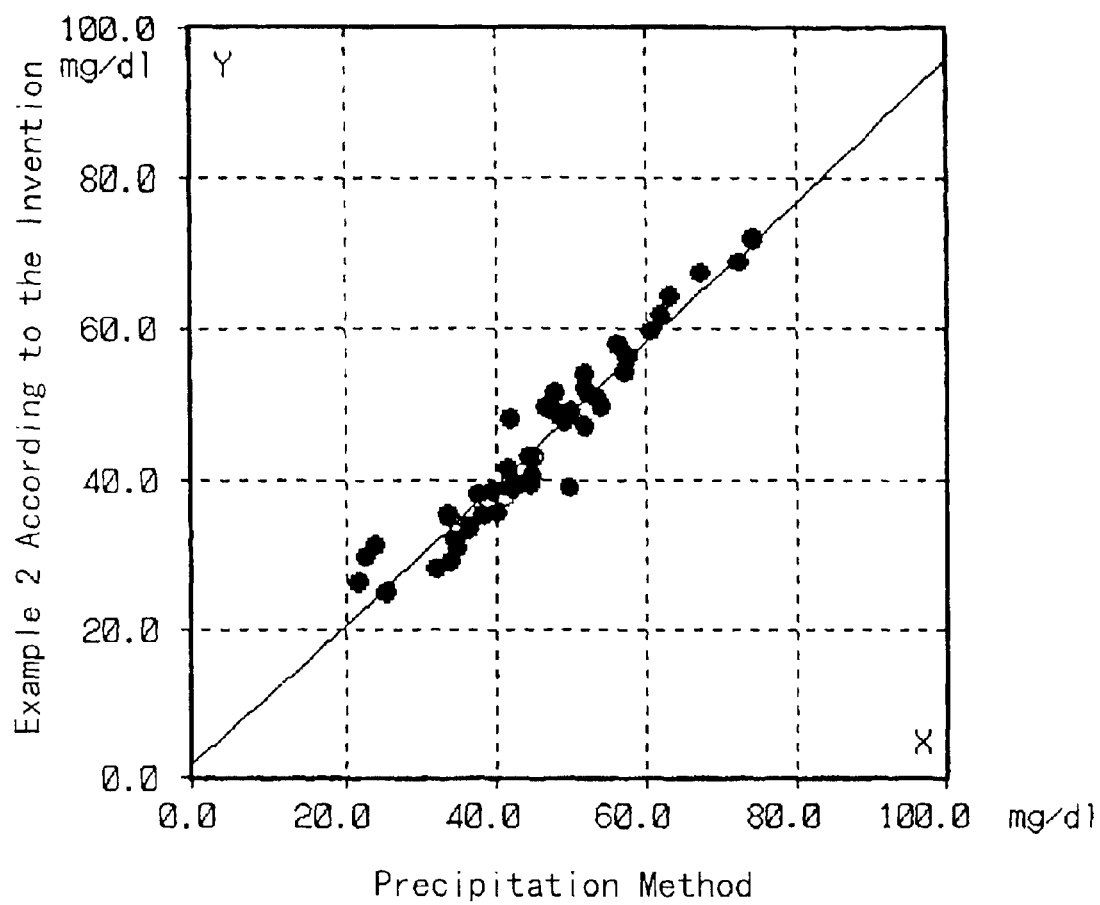
FIG. 1 shows correlation between the amounts of the cholesterol in HDL measured by the method of an example according to the present invention and the amounts of the cholesterol in HDL measured by the conventional precipitation method.

Cholesterols contained in lipoproteins include ester type cholesterol (cholesterol ester) and free cholesterol. In this specification, the term "cholesterol" includes both of these unless otherwise specified.

The test sample subjected to the method of the present invention may be any sample which may contain lipoproteins such as HDL, LDL, VLDL and CM. Examples of the test samples include body fluids such as sera as well as dilutions thereof, although the test samples are not restricted thereto.

In the first step in the method of the present invention, the cholesterol in the lipoproteins other than HDL in the test sample is selectively erased. The term "erase" herein means to decompose the cholesterol and to make the decomposed products undetectable in the subsequent second step. The methods for selectively erasing the cholesterol in the lipoproteins other than HDL, that is, in LDL, VLDL, CM and the like include the following methods.

In the first method, cholesterol esterase and cholesterol oxidase are acted on the test sample in the absence of a surfactant which acts on HDL, and the generated hydrogen peroxide is removed. By the action of cholesterol esterase, the ester type cholesterol in the lipoproteins are hydrolyzed to yield free cholesterol and fatty acids. The thus generated free cholesterol and the free cholesterol inherently existing in the lipoproteins are oxidized by the action of cholesterol oxidase to yield cholestenone and hydrogen peroxide. The thus generated hydrogen peroxide is removed. Methods for removing hydrogen peroxide include a method in which the hydrogen peroxide is decomposed to water and oxygen by catalase; and a method in which a phenol-based or aniline-based hydrogen donor compound, such as DAOS (N-ethyl-N-(2-hydroxysulfopropyl)-3,5-dimethoxyaniline), which reacts with hydrogen peroxide to yield a colorless quinone, is reacted with the hydrogen peroxide to convert the hydrogen peroxide to the colorless quinone, although the methods for removing hydrogen peroxide are not restricted to these methods.

In the above-mentioned first step, by carrying out the step in the absence of a surfactant which acts on HDL, the cholesterol in HDL is not substantially reacted, while the cholesterol in the other lipoproteins such as LDL, VLDL and CM are reacted and erased. By this, in the subsequent second step, the cholesterol in HDL is selectively quantified.

The concentration of the cholesterol esterase in the reaction mixture in the first step may preferably be about 0.2 to 1.0 U/ml, and the concentration of the cholesterol oxidase may preferably be about 0.1 to 0.7 U/ml. The concentration of the catalase may preferably be about 40 to 100 U/ml and the concentration of the peroxidase may preferably be about 0.4 to 1.0 U/ml. The concentration of the compound which yields the colorless quinone upon reaction with hydrogen peroxide may preferably be about 0.4 to 0.8 mmol/l.

The reaction in the first step may preferably be carried out in a buffer with a pH of 5 to 8, and the buffer may preferably be phosphate buffer, glycine buffer, Tris buffer or Good's buffer. Especially, Bis-Tris, PIPES, MOPSO, BES, HEPES and POPSO which are Good's buffer are preferred. The concentration of the buffer may preferably be about 10 to 500 mM.

To increase the degree of erasing of the lipoproteins other than HDL, divalent metal ion may be contained in the reaction mixture. Preferred examples of the divalent metal ion include copper ion, iron ion and magnesium ion. Among these, magnesium ion is especially preferred. The concentration of the divalent metal ion may preferably be about 5 to 200 mM.

A lipoprotein hydrolase may optionally be added to the reaction mixture in the first step. Addition of this enzyme is preferred because especially the cholesterol in VLDL easily reacts. The concentration of this enzyme in the reaction mixture may preferably be about 5.0 to 10.0 U/ml.

The reaction temperature in the first step may preferably be about 25° C. to 40° C., and 37° C. is best preferred. The reaction time may be about 2 to 10 minutes.

In the following second step, a surfactant which specifically acts on HDL is added to the reaction product of the first step, and the cholesterol in high density lipoprotein is enzymatically quantified. The term "surfactant which specifically acts on HDL" means a surfactant by which the cholesterol in HDL reacts due to the action of an enzyme such as cholesterol esterase or cholesterol oxidase (the reaction ratio is not less than 70%, preferably not less than 90%), while the cholesterol in the lipoproteins other than HDL does not substantially react (the reaction ratio is not more than 30%, preferably not more than 20%). Examples of such a surfactant include the surfactants having a hydrophilicity lipophilicity balance (HLB) of 13 to 14, especially nonionic surfactants with a HLB of 13 to 14, especially polyalkylene oxide derivatives. Preferred examples of the derivatives here include condensation products with higher alcohols, condensation products with higher fatty acids, condensation products with higher fatty acid amides, condensation products with higher alkylamines, condensation products with higher alkylmercaptane and condensation products with alkyl phenols. Among the polyalkyleneoxide derivatives, polyethylene oxide derivatives are best preferred. The above-mentioned range of HLB may be attained by mixing a plurality of surfactants, and such a mixture of a plurality of surfactants may also be used. The method for calculating HLB of surfactants is well-known, and is described in, for example, Hiroshi HORIGUCHI, "New Surfactants", 1986, Sankyo Shuppan.

Preferred specific examples of the surfactant include polyoxyethylene lauryl ether, polyoxyethylene cetyl ether, polyoxyethylene oleyl ether, polyoxyethylene higher alcohol ($C_4$–$C_{35}$) ether, polyoxyethylene octyl phenyl ether, polyoxyethylene nonylphenyl ether and the like, although the surfactant is not restricted thereto.

Although the concentration of the surfactant in the second step is not restricted, it may preferably be 0.05 to 3% by weight, more preferably 0.1 to 1.5% by weight based on the total reaction mixture.

In the presence of the above-mentioned surfactant, the HDL cholesterol in the test sample may be enzymatically quantified. That is, in the first step, most of the cholesterol in the lipoproteins other than HDL is erased, and with the synergistic effect with the reaction in the second step, the cholesterol in HDL alone is quantified.

The method for enzymatically quantify cholesterol per se is well-known in the art. For example, as in the first step, cholesterol may be quantified by generating hydrogen peroxide from cholesterol ester and free cholesterol by the action of cholesterol esterase and cholesterol oxidase, and by quantifying the generated hydrogen peroxide. Quantification of hydrogen peroxide may be carried out by, for example, reacting the hydrogen peroxide with a compound which forms a quinone pigment, and by measuring the amount of the generated quinone pigment by measuring absorbance or the like. The quinone pigment may be formed by, for example, reacting hydrogen peroxide and 4-aminoantipyrine and DAOS or HDAOS (N-(2-hydroxysulfopropyl)-3,5-dimethyoxyaniline). The quinone pigment formed thereby has the maximum absorbance at 593 nm when DAOS is used, and has the maximum absorbance at 583 nm when HDAOS is used. Although the concentration of the compound which yields the quinone pigment is not restricted, the concentration of 4-aminoantipyrine, for example, may preferably be 0.1 to 2.0 mM, more preferably 0.5 to 1.5 mM, and the concentration of DAOS or HDAOS may preferably be 0.1 to 1.5 mM, more preferably 0.4 to 1.0 mM. Although the concentration of the peroxidase is not restricted, it may preferably be 0.4 to 5 U/ml in the total reaction mixture. Preferred reaction conditions (reaction temperature, reaction time, buffer and pH) are the same as the preferred reaction conditions in the first step.

In cases where the generated hydrogen peroxide is decomposed with catalase, a catalase inhibitor such as sodium azide is used in the second step so as to inhibit the catalase because it is necessary to inhibit the catalase in the second step.

EXAMPLES

The present invention will now be described more concretely by way of examples thereof. It should be noted, however, the present invention is not restricted to the examples below. In the examples below, all "%" are by weight unless otherwise specified.

Reference Example 1

Using samples containing known amounts of purified HDL, LDL, VLDL and CM, respectively, the cholesterol in each of the lipoproteins was enzymatically quantified in the presence of a nonionic surfactant Emulgen 911 (polyoxyethylene nonyl ether, HLB 13.7), Emulgen B66 (polyoxyethylene derivative, HLB 13.2) or a mixture of Emulgen B66 and Emulgen A90 (polyoxyethylene derivative, HLB 14.5), all of which are commercially available from KAO CORPORATION. This operation was carried out as follows.

To a solution containing 0.5 U/ml cholesterol esterase, 0.4 U/ml cholesterol oxidase, 0.5 U/ml peroxidase, 1.0 mmol/l 4-aminoantipyrine and 0.5 mmol/l HDAOS in 50 mM PIPES buffer, pH 7.0, Emulgen 911 or Emulgen B66 was added to a concentration of 0.1% by weight, or Emulgen B66/Emulgen A90 mixture (9/1) was added to a concentration of 1.3% by weight. Twenty microliters of each sample was mixed with 2.0 ml of the thus prepared mixture and the resulting mixture was allowed to react at 37° C. for 10 minutes, followed by measuring absorbance at 600 nm.

As a result, the reaction ratio (i.e., the ratio of the quantified cholesterol in the total cholesterol) was about 95% for the cholesterol in HDL, and about 18 to 22% for the cholesterols in other lipoproteins.

From this, it can be seen that Emulgen 911, Emulgen B66 and the Emulgen B66/Emulgen A90 mixture are within the scope of the term "surfactant which specifically acts on high density lipoprotein".

Example 1

First reagents and second reagents having the following compositions, respectively, were prepared.

| First Reagents | |
| --- | --- |
| PIPES buffer, pH 7.0 | 100 mmol/l |
| HDAOS | 0.7 mmol/l |
| Cholesterol esterase | 0.8 U/ml |
| Cholesterol oxidase | 0.5 U/ml |
| Catalase | 80 U/ml |
| Magnesium chloride | 10 mmol/l |
| Second Reagents | |
| PIPES buffer, pH 7.0 | 100 mmol/l |
| 4-aminoantipyrine | 4.0 mmol/l |
| Peroxidase | 2.4 U/ml |
| Sodium azide | 0.1% |
| Emulgen B66 (HLB13.2) commercially available from KAO CORPORATION | 0.3% |

To each of 4 samples having a volume of 4 μl containing purified HDL, LDL, VLDL and CM at a concentration of 100 mg/dl, respectively, 300 μl of the above-described first reagents which had been preliminarily warmed at 37° C. were added and each of the resulting mixtures was allowed to react at 37° C. for 5 minutes. Thereafter, 100 μl of the second reagents were added to each mixture and each of the resultants was allowed to react for 5 minutes, followed by measurement of absorbance of each reaction mixture at 600 nm. Based on the measured absorbances, the amounts of cholesterol were calculated and the ratio of the thus calculated amount to the amount of the cholesterol in the sample was calculated, which is defined as capture ratio.

By this method, the hydrogen peroxide produced in the first step is decomposed by catalase. On the other hand, the hydrogen peroxide generated in the second step forms a quinone pigment by reacting with HDAOS and 4-aminoantipyrine. The results are shown in Table 1.

TABLE 1

| Capture Ratio | | | |
| --- | --- | --- | --- |
| CM | VLDL | LDL | HDL |
| <1.0% | <1.0% | <1.0% | 86.6% |

As shown in Table 1, by the above-described method, most of the cholesterol in HDL is quantified. On the other hand, the cholesterol in the lipoproteins other than HDL is not substantially quantified. Thus, it can be seen that the cholesterol in HDL can be selectively quantified by the method of the present invention.

Example 2

Cholesterol in HDL in test samples was quantified by the same method as in Example 1 except that the test samples were sera of normal individuals. On the other hand, the HDL cholesterol in the same test samples was quantified by the precipitation method described in "Clinical Tests", 23, 121 (1979). The correlation between the results obtained by these methods is shown in FIG. 1.

As shown in FIG. 1, the results of the quantification by these methods well matched, so that it was proved that the cholesterol in HDL can be accurately quantified by the method of the present invention.

Example 3

The same procedure as in Example 1 was repeated except that the first and second reagents had the following compositions, respectively.

| First Reagents | |
|---|---|
| HEPES buffer, pH 7.0 | 50 mmol/l |
| DAOS | 1.5 mmol/l |
| Cholesterol esterase | 0.8 U/ml |
| Cholesterol oxidase | 0.5 U/ml |
| Peroxidase | 1.0 U/ml |
| Second Reagents | |
| HEPES buffer, pH 7.0 | 50 mmol/l |
| 4-aminoantipyrine | 4.0 mmol/l |
| Emulgen 911 (HLB13.7) commercially available from KAO CORPORATION | 0.3% |

By this method, the hydrogen peroxide produced in the first step reacts with DAOS by the action of peroxidase to form a colorless quinone. On the other hand, the hydrogen peroxide generated in the second step reacts the remaining DAOS from the first step and with 4-aminoantipyrine added in the second step by the action of peroxidase to form a quinone pigment. The results are shown in Table 2.

TABLE 2

| Capture Ratio | | | |
|---|---|---|---|
| CM | VLDL | LDL | HDL |
| <1.0% | <1.0% | <1.0% | 85.3% |

As shown in Table 2, by the above-described method, most of the cholesterol in HDL is quantified. On the other hand, the cholesterol in the lipoproteins other than HDL is not substantially quantified. Thus, it can be seen that the cholesterol in HDL can be selectively quantified by the method of the present invention.

Example 4

Cholesterol in HDL in test samples was quantified by the same method as in Example 3 except that the test samples were sera of normal individuals. As in Example 2, the HDL cholesterol in the same test samples was quantified by the precipitation method. The correlation between the results obtained by these methods is shown in FIG. 2.

Figure 2:
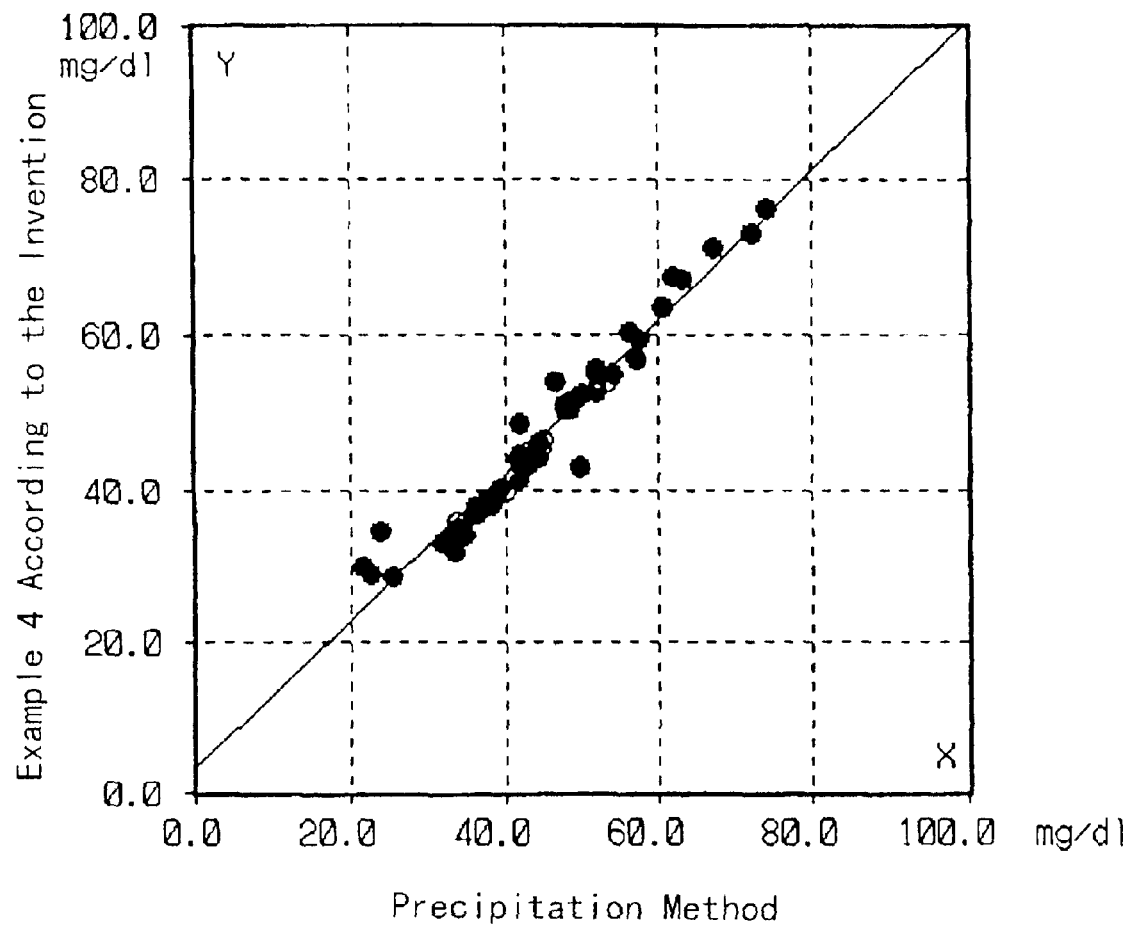
FIG. 2 shows correlation between the amounts of the cholesterol in HDL measured by the method of another example according to the present invention and the amounts of the cholesterol in HDL measured by the conventional precipitation method.

As shown in FIG. 2, the results of the quantification by these methods well matched, so that it was proved that the cholesterol in HDL can be accurately quantified by the method of the present invention.

Example 5

First reagents and second reagents having the following compositions, respectively, were prepared.

| First Reagents | |
|---|---|
| BES buffer, pH 7.0 | 100 mmol/l |
| HDAOS | 0.7 mmol/l |
| Cholesterol esterase | 0.8 U/ml |
| Cholesterol oxidase | 0.5 U/ml |
| Catalase | 100 U/ml |
| Magnesium chloride | 18 mmol/l |
| Second Reagents | |
| BES buffer, pH 7.0 | 100 mmol/l |
| 4-aminoantipyrine | 4.0 mmol/l |

-continued

| | |
|---|---|
| Peroxidase | 2.4 U/ml |
| Sodium azide | 0.1% |
| Emulgen B66 (HLB13.2) commercially available from KAO CORPORATION | 1.17% |
| Emulgen A90 (HLB14.5) commercially available from KAO CORPORATION | 0.13% |

To each of 4 samples having a volume of 4 μl containing purified HDL, LDL, VLDL and CM at a concentration of 100 mg/dl, respectively, 300 μl of the above-described first reagents which had been preliminarily warmed at 37° C. were added and each of the resulting mixtures was allowed to react at 37° C. for 5 minutes. Thereafter, 100 μl of the second reagents were added to each mixture and each of the resultants was allowed to react for 5 minutes, followed by measurement of absorbance of each reaction mixture at 600 nm. Based on the measured absorbances, the amounts of cholesterol were calculated and the ratio of the thus calculated amount to the amount of the cholesterol in the sample was calculated, which is defined as capture ratio.

By this method, the hydrogen peroxide produced in the first step is decomposed by catalase. On the other hand, the hydrogen peroxide generated in the second step forms a quinone pigment by reacting with HDAOS and 4-aminoantipyrine. The results are shown in Table 3.

| Capture Ratio | | | |
|---|---|---|---|
| CM | VLDL | LDL | HDL |
| <1.0% | <1.0% | <1.0% | 98.0% |

As shown in Table 3, by the above-described method, most of the cholesterol in HDL is quantified. On the other hand, the cholesterol in the lipoproteins other than HDL is not substantially quantified. Thus, it can be seen that the cholesterol in HDL can be selectively quantified by the method of the present invention.

Example 6

Cholesterol in HDL in test samples was quantified by the same method as in Example 5 except that the test samples were sera of normal individuals. On the other hand, the HDL cholesterol in the same test samples was quantified by the precipitation method described in "Clinical Tests", 23, 121 (1979). The correlation between the results obtained by these methods is shown in FIG. 3.

Figure 3:
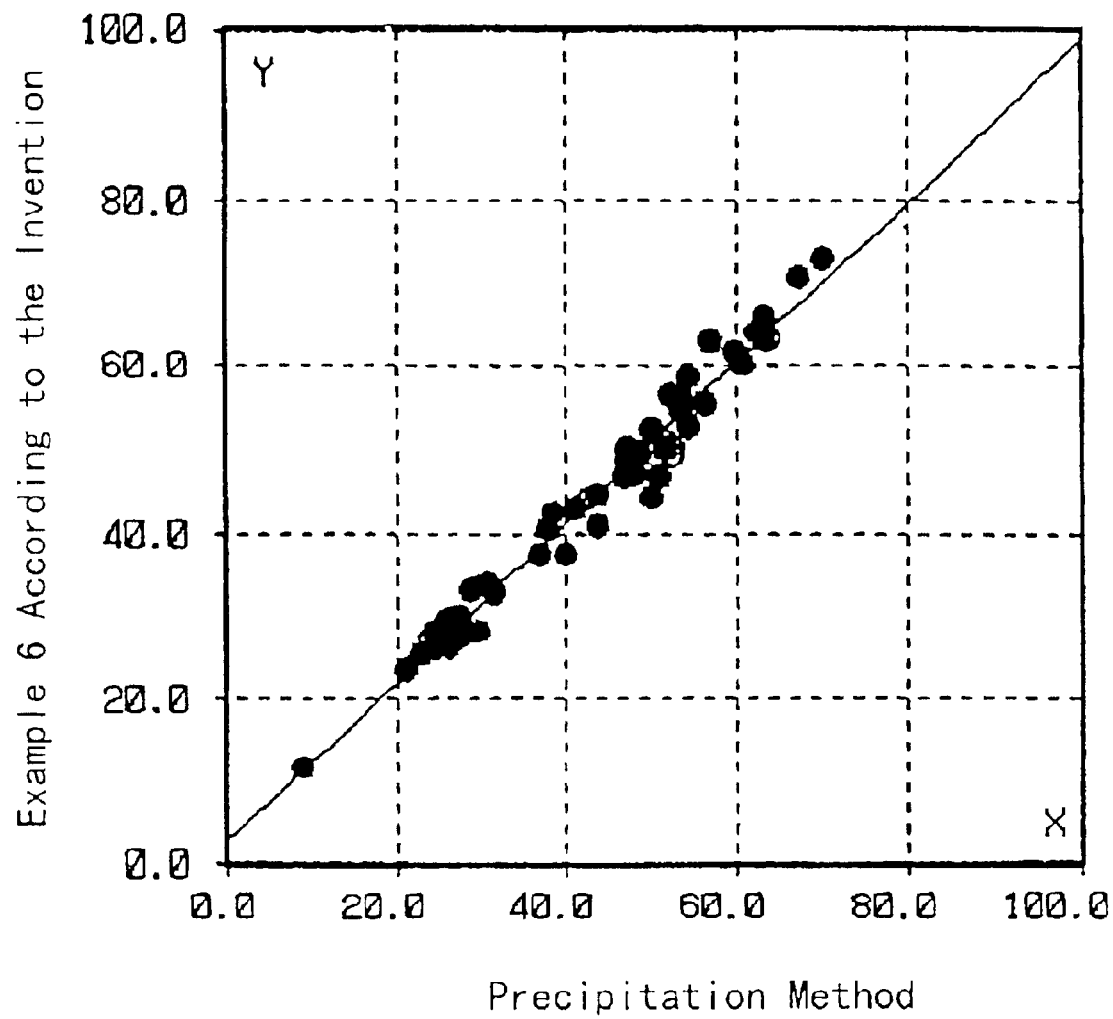
FIG. 3 shows correlation between the amounts of the cholesterol in HDL measured by the method of a still another example according to the present invention and the amounts of the cholesterol in HDL measured by the conventional precipitation method.

As shown in FIG. 3, the results of the quantification by these methods well matched, so that it was proved that the cholesterol in HDL can be accurately quantified by the method of the present invention.

What is claimed:

1. A method for enzymatically quantifying cholesterol in high density lipoprotein, comprising the steps of reacting a surfactant which specifically acts on high density lipoprotein with the high density lipoprotein, and enzymatically quantifying cholesterol in said high density lipoprotein; wherein the surfactant substantially does not act on other lipoproteins.

2. The method according to claim 1, wherein said surfactant which specifically acts on high density lipoprotein has a hydrophilicity lipophilicity balance (HLB) of 13–14.

3. A method for enzymatically quantifying cholesterol in high density lipoprotein, comprising the steps of reacting a surfactant which specifically acts on high density lipoprotein with the high density lipoprotein, and enzymatically quantifying cholesterol in said high density lipoprotein; wherein said surfactant which specifically acts on high density lipoprotein is a polyalkylene oxide derivative.

4. The method according to claim 2, wherein said surfactant which specifically acts on high density lipoprotein is a polyalkylene oxide derivative.

* * * * *